United States Patent [19]

Davis et al.

[11] Patent Number: 5,544,661
[45] Date of Patent: Aug. 13, 1996

[54] REAL TIME AMBULATORY PATIENT MONITOR

[75] Inventors: Charles L. Davis, 16830 SW. Spellman Dr., Beaverton, Oreg. 97007; Paul V. Long, Newberg, Oreg.

[73] Assignee: Charles L. Davis, Beaverton, Oreg.

[21] Appl. No.: 180,867

[22] Filed: Jan. 13, 1994

[51] Int. Cl.$^6$ ............................................... A61B 5/0402
[52] U.S. Cl. ........................................... 128/700; 128/904
[58] Field of Search .................................... 128/903, 904, 128/905, 700, 696, 672, 674

[56] References Cited

U.S. PATENT DOCUMENTS

| | | | |
|---|---|---|---|
| 4,706,689 | 11/1987 | Man | 128/903 |
| 5,038,800 | 8/1991 | Oba | 128/904 |
| 5,113,869 | 5/1992 | Nappholz et al. | 128/903 |
| 5,348,008 | 9/1994 | Bornn et al. | 128/904 |

*Primary Examiner*—William E. Kamm
*Assistant Examiner*—Scott M. Getzow
*Attorney, Agent, or Firm*—Marger, Johnson, McCollom & Stolowitz, P.C.

[57] ABSTRACT

A patient monitoring system which includes a portable device and a central station. The portable device includes an ECG and a photo-plethysmograph connected to the patient; arrhythmia analysis apparatus; an expert system for determining if a pre-established critical parameter set has been exceeded; and a wireless wide area communication device for automatically contacting the central station via a public cellular phone network when the critical parameter set has been exceeded. When the central station is contacted, the patient's ECG waveforms, measurements, and trends, are sent to the central monitoring station and a two way voice channel between the patient and the central station is automatically opened. The central station includes a computerized facility which has a station from which a clinician can observe the real time data being sent from the patient, the patients historical records and from which the clinician can talk to the patient and activate therapeutic devices attached to the patient such as an external defibrillator, a pacer or an automatic drug infusion device.

12 Claims, 15 Drawing Sheets

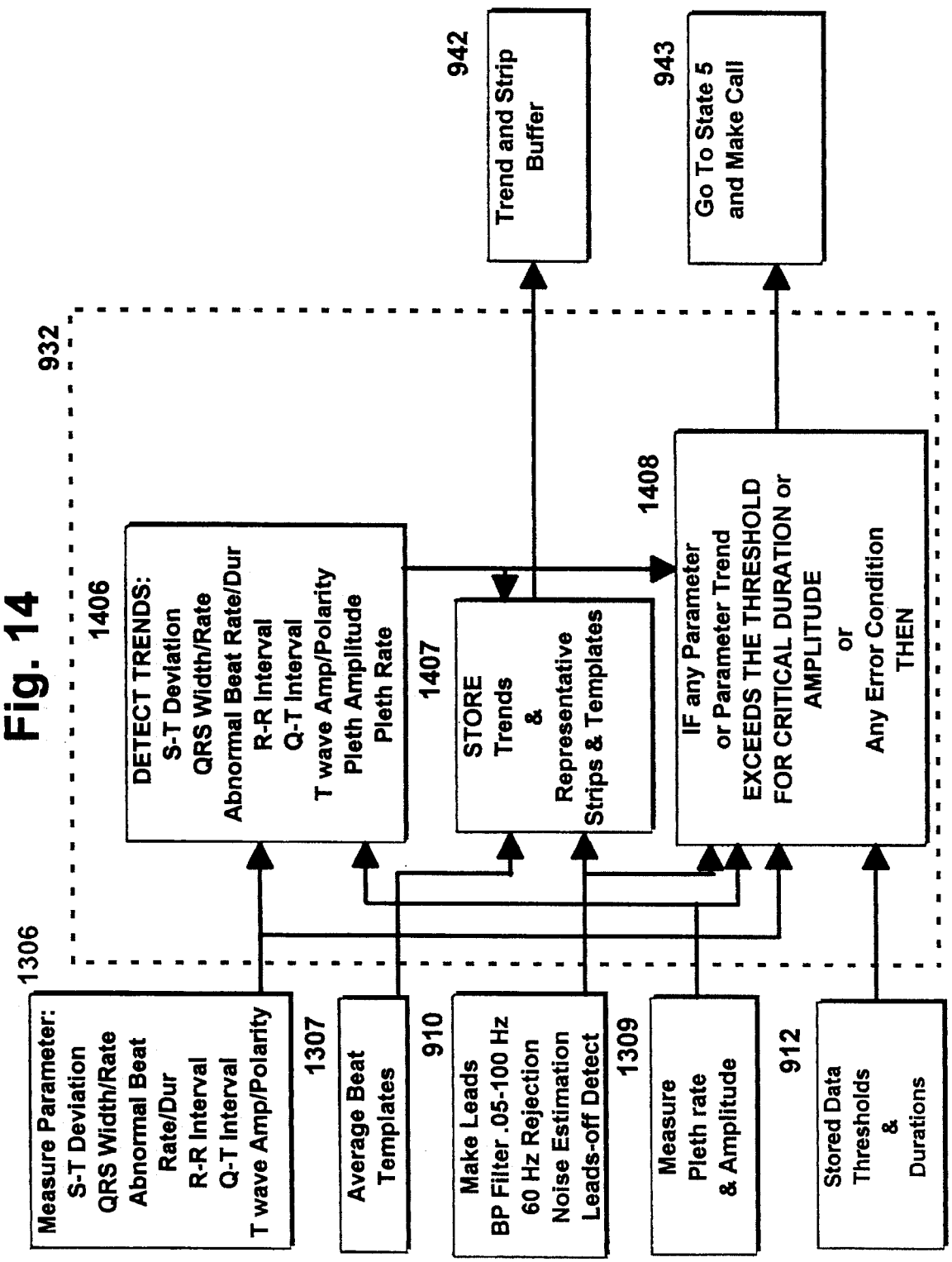

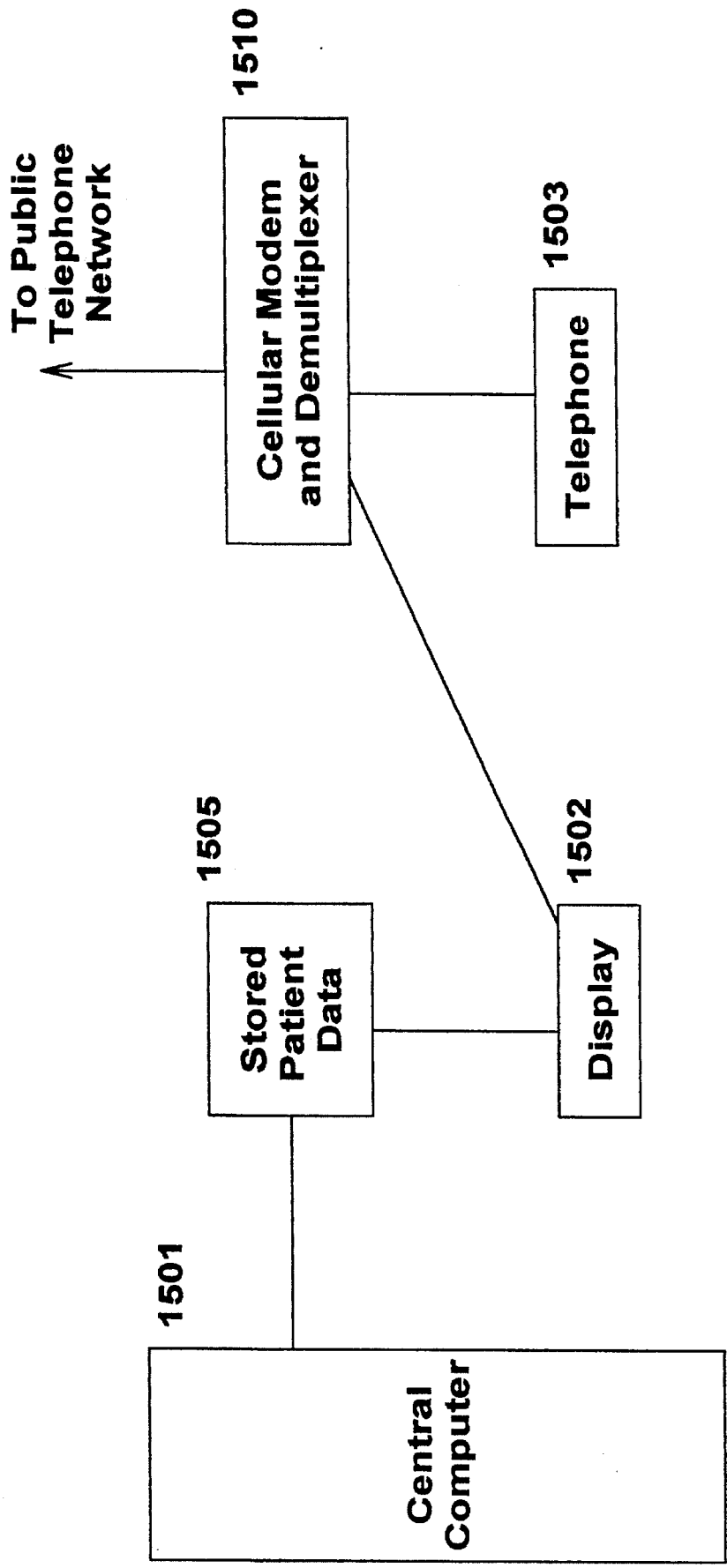

REAL TIME AMBULATORY PATIENT MONITOR

FIELD OF THE INVENTION

The present invention relates to a method and apparatus for monitoring the physical condition of a patient and for automatically notifying a central monitor if the patient's condition requires attention.

BACKGROUND OF THE INVENTION

Quick action is often essential when a high risk cardiac patient experiences a warning or life threatening arrhythmia. At the present time hospitalization is often required in order to continuously monitor a patient's electrocardiogram (ECG) and quickly detect any warning or life threatening arrhythmias. The cost of hospitalization is very high and thus it is highly desirable to monitor a patient's condition on an outpatient basis rather than having the patient hospitalized.

A wide variety of apparatus has been developed to monitor a patient's ECG outside of a hospital environment. However, the presently available out-patient monitoring apparatus has a variety of deficiencies. Some out-patient monitoring apparatus, such as holter devices, merely record the patient's ECG for examination at a later time. Some present day out-patient monitoring apparatus, such as event monitors) require the patient to take action when an arrhythmia occurs in order to record an ECG which is later transmitted to a clinician. Still other present day out-patient monitoring apparatus has a limited range, thus the patient must stay close to a base station.

While monitoring equipment has been described in the literature which is supposed to allow patients to be discharged from hospitals sooner than they would have been discharged without such equipment, many cardiac patients are still hospitalized for relatively long periods of time merely for the purpose of monitoring their condition and to insure that any arrhythmias are quickly detected and appropriate action taken.

The present invention is directed to an improved out-patient monitoring device which detects arrhythmias or other ECG morphology changes along with other physiological indications, and immediately notifies a central monitoring station without any action on the part of the patient. A clinician at the central station can be put into voice contact with the patient. Monitoring proceeds while additional data is being transmitted to the clinician. The present invention can also be applied to inpatient monitoring systems to improve monitoring efficiency.

With the present invention the clinician at the central station has both voice contact with the patient and access to the patient's current ECG and photoplethysmograph. The clinician can activate one or more interventional therapeutic devices attached to the patient such as an external defibrillator, a pacer or a drug infusion device. Furthermore the clinician can change various parameters, settings, or programs in the patient monitoring device on a real time basis.

SUMMARY OF THE INVENTION

A patient monitoring system which includes a portable device and a central station. The portable device includes an ECG and a photoplethysmograph connected to the patient; arrhythmia analysis apparatus; an expert system for determining if a pre-established critical parameter set has been exceeded; and a wireless communication device for automatically contacting the central station via a public cellular phone network when the critical parameter set has been exceeded. When the central station is contacted, the patient's ECG waveforms, measurements, and trends, are sent to the central monitoring station and a two way voice channel between the patient and the central station is automatically opened. The central station includes a computerized facility which has a station from which a clinician can observe the real time data being sent from the patient, the patients historical records and from which the clinician can talk to the patient and activate therapeutic devices attached to the patient such as an external defibrillator, a pacer or an automatic drug infusion device.

BRIEF DESCRIPTION OF DRAWINGS

FIG. 14 is a block diagram that shows the programmed operations that take place during the analysis operation.

FIG. 15 is a block diagram of the central monitoring station.

DESCRIPTION OF A PREFERRED EMBODIMENT

Figure 1:
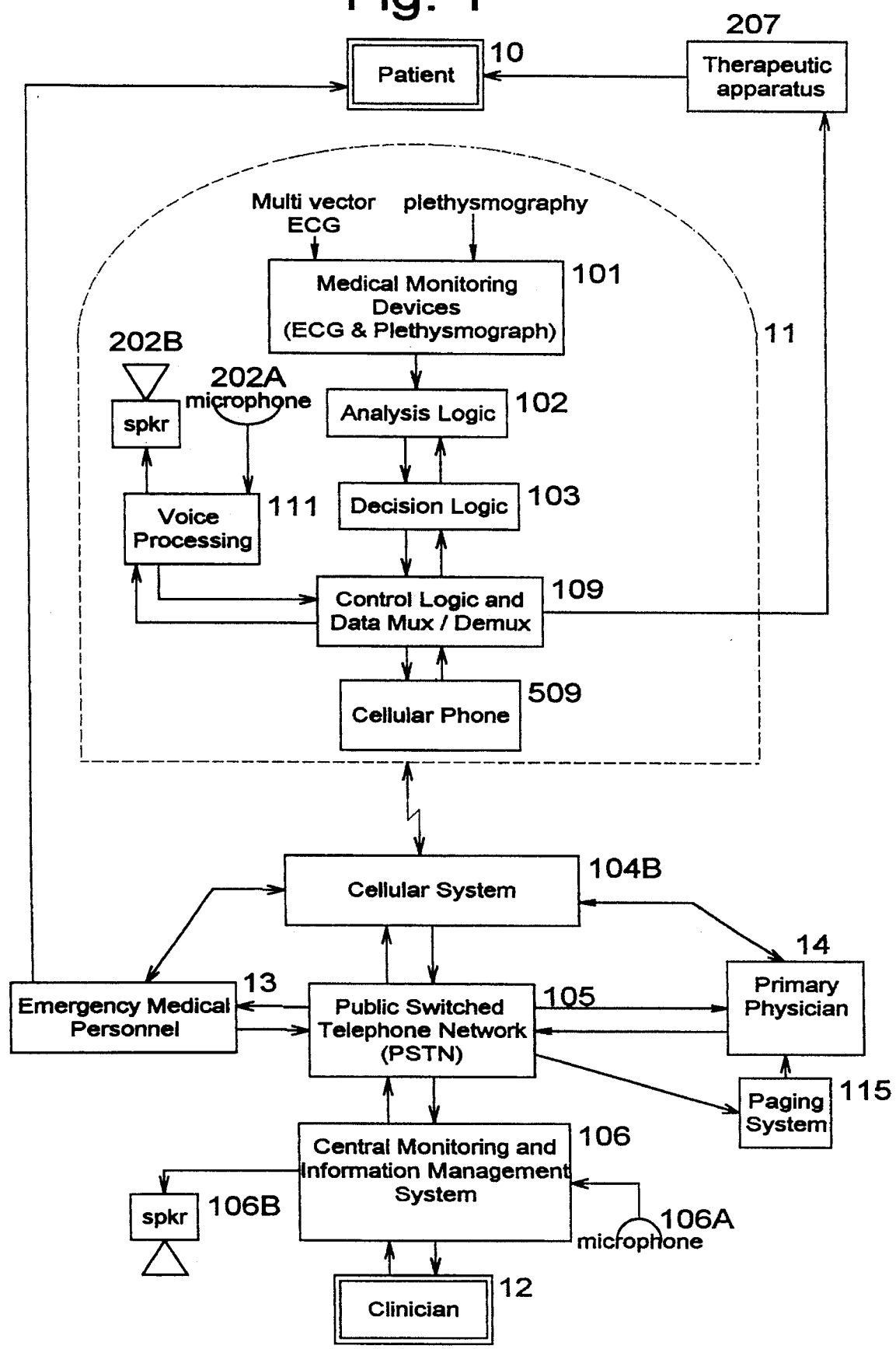
FIG. 1 is an overall block diagram of the preferred embodiment of the invention which is described herein.

FIG. 1 is an overall block diagram of a preferred embodiment of the invention. As shown in FIG. 1 with the preferred embodiment of the invention shown and described herein a patient 10 is monitored and automatically connected to a clinician 12 when a warning or life threatening arrhythmias or other event requiring emergency attention occurs. A portable monitoring, processing and cellular phone unit 11 is attached to patient 10. Monitoring, processing and cellular phone unit 11 includes an ECG and a plethysmograph 101. The unit 11 continuously monitors the condition of patient 10.

Data from the ECG and the plethysmograph 101 is fed into analysis logic 102. Analysis logic 102 is a programmed microprocessor which can perform a wide variety of analysis. The output of the analysis logic 102 goes to decision logic 103 which compares the patient data to certain preset parameters. If the patient's data is outside the preset parameters, cellular phone 509 is activated by controller logic 109. Cellular phone 509 is a conventional cellular phone which operates with cellular system 104B and through the public network 105. The cellular phone dials into the central monitoring station 106 whenever the patient's condition is outside the preset parameters. The patient's ECG waveform, calculated metrics, trends, measurements made by the plethysmograph, and the stored ECG and plethysmograph strips are sent to the central station 106 through the cellular phone 509 and 104B and the public network 105. A clinician 12 located at the central station can observe the patient's physiological data and the clinician can also voice communicate with the patient or someone proximate to the patient over the same public network 105 and cellular communication channel 509 and 104B that is transmitting the data to the central monitoring station 106.

If the patient requires emergency care, the clinician 12 can notify an emergency medical personnel 13 through public switched telephone network 105 and give the patient's location and condition. The emergency personnel 13 can then travel to the patient 10 and deliver medical care. The clinician 12 may also alert the primary care physician 14 via public network 105 so that physician 14 may intercept the patient 10 at the hospital. The physician 14 may also be notified via pager 115.

Figure 2:
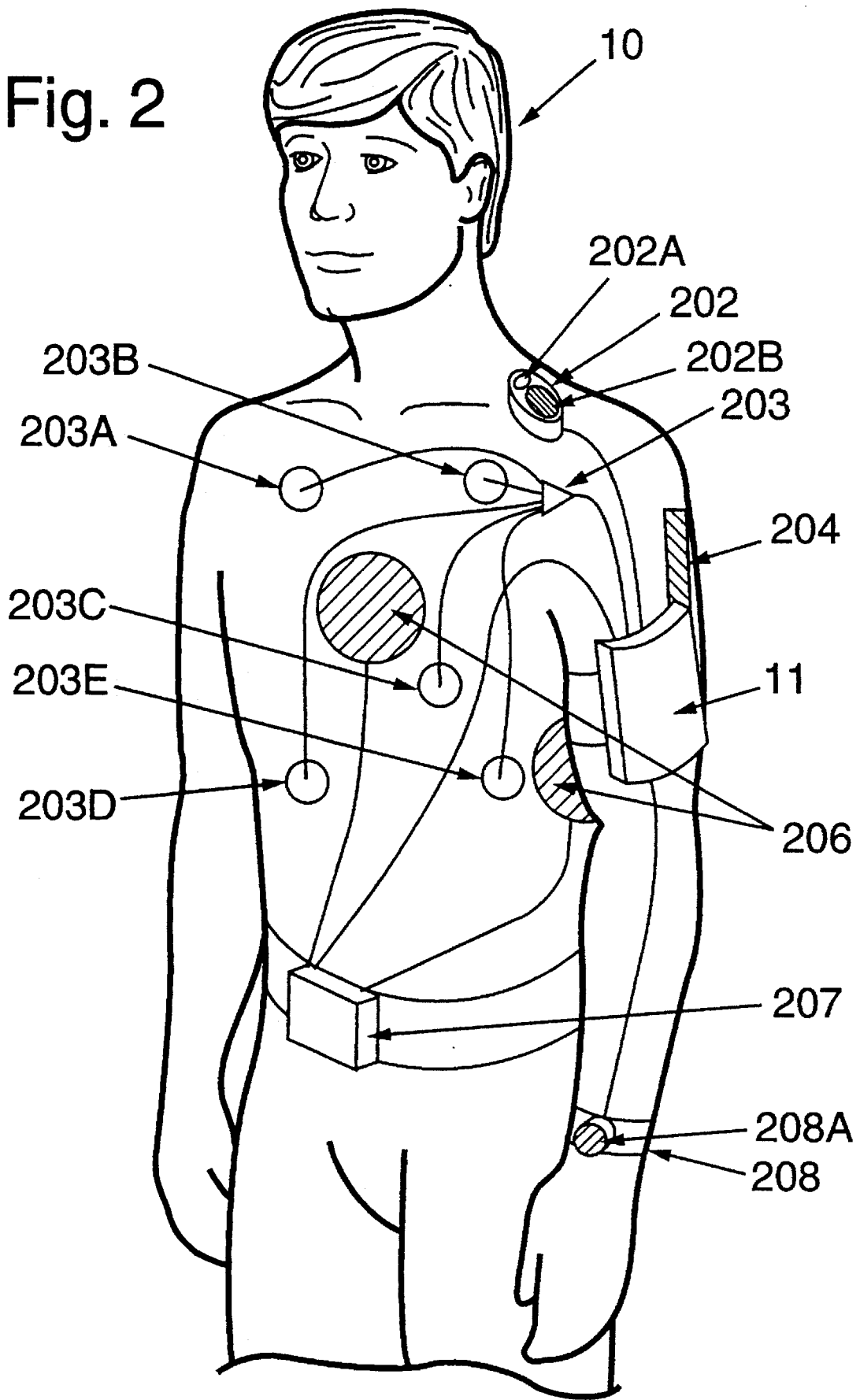
FIG. 2 is a diagram showing the devices worn by the patient.

FIG. 2 shows the apparatus worn by the patient 10. The apparatus worn by the patient 10 includes (a) processing, data acquisition, control and cellular phone unit 11, (b) ECG pads 203A to 203E which are connected to unit 11 via a cable 203, (c) photo-plethysmograph probe 208 which is attached to the patient 10 by a wriststrap 208A, (d) a defibrillation unit 207 which has defibrillation pads 206A and 206B, and (e) a speaker 202A and (f) a microphone 202B. Each of the devices worn by the patient 10 are connected by wires to unit 11. A conventional cellular phone antenna 204 is connected to unit 11. For convenience of illustration the shoulder and arm harness which holds unit 11 on the patient's body are not shown in FIG. 2. The exact configuration of the harness and arm strap are not particularly relevant to the present invention and they can take a wide variety of forms including simple pieces of adhesive tape or an arm strap and shoulder harness made from elastic fabric material. Defibrillation unit 207 is attached to a belt 207A which is worn around the patient's waist.

Figure 3:
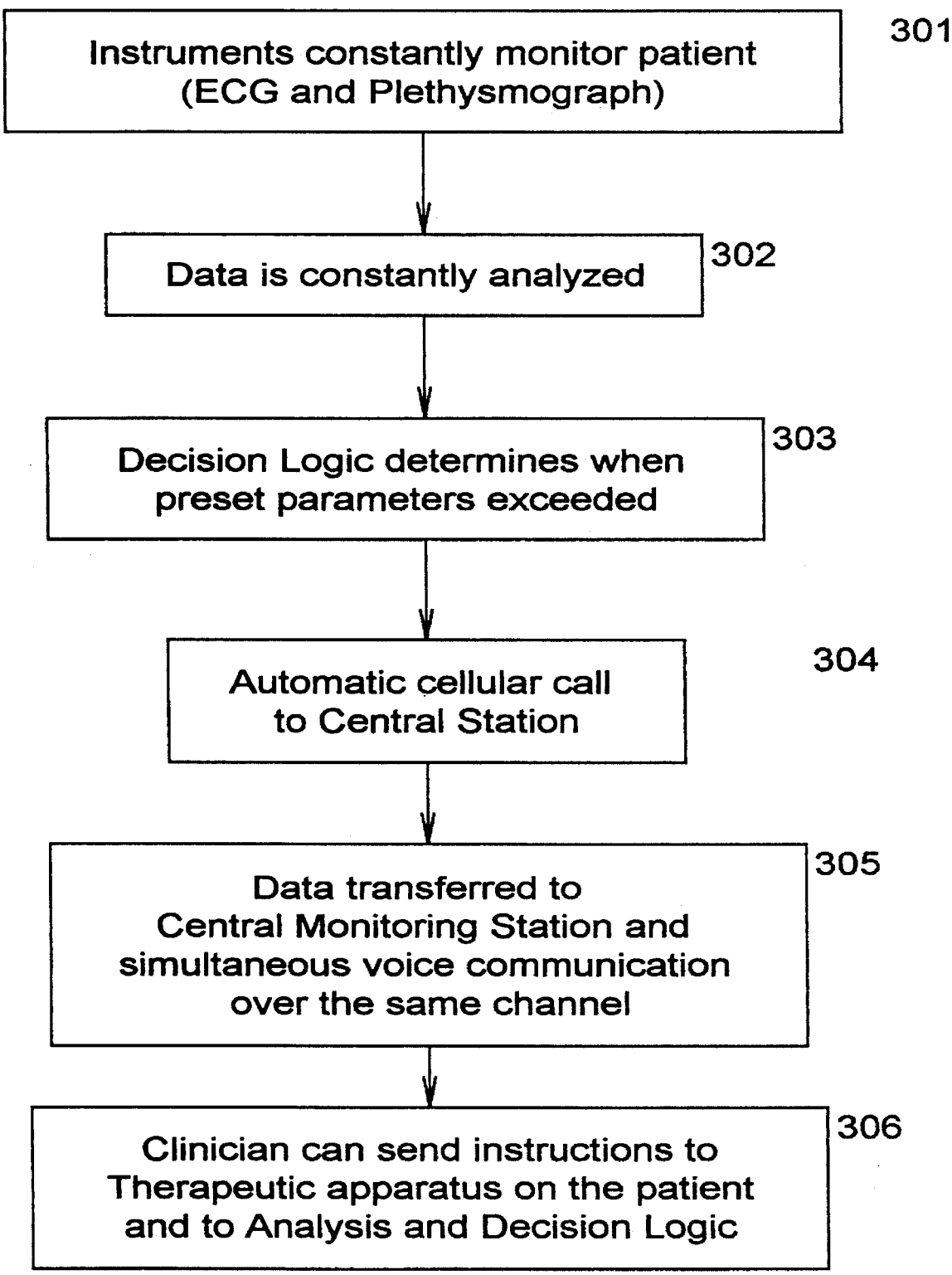
FIG. 3 is a flow diagram showing the major steps in the operation of the preferred embodiment.

FIG. 3 is a general flow diagram showing the major steps in the operation of the present invention. As indicated by block 301, the ECG 203A to 203E and the plethysmograph 208 constantly monitor the patient's condition. The data from the instruments connected to the patient is constantly analyzed (block 302) and the data that is generated by the analysis is sent to decision logic 103 (block 303) which compares the patent's data to preset parameters to determine if the patient is experiencing a warning or life threatening arrhythmia or other conditions requiring emergency attention. Block 304 indicates that if the decision logic 103 determines that the patient is experiencing an emergency condition, an automatic call is placed to the central station 106. As indicated by block 305, data is transferred to the Central monitoring station 106 over the cellular phone 509 and 104B and public network 105 connection. The cellular phone 509 and 104B and public network 105 connection is used to transmit data and voice and thus the clinician and patient can carry on a voice conversation over the same communication channel that is being used to transmit the patient's data. Finally as indicated by block 306, the clinician 12 can send instructions which activate the therapeutic apparatus 207 worn by the patient. In the preferred embodiment shown herein the therapeutic apparatus 207 comprises a defibrillator. The clinician 12 can also send a new set of parameters to the decision logic 103 or a new analysis program to the analysis logic 102.

Figure 4:
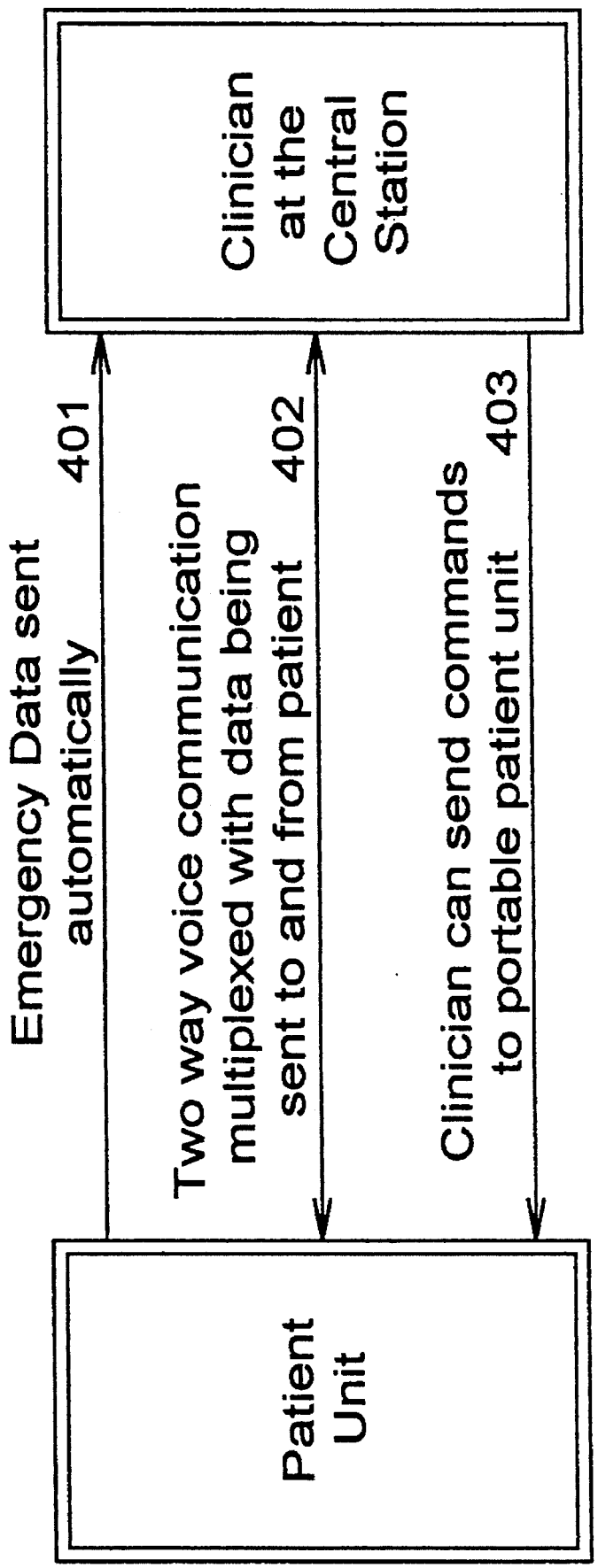
FIG. 4 is a diagram showing the data paths between the patient and the clinician.

FIG. 4 shows the communication paths between the portable patient unit 11 attached to patient 10 and the clinician 12 who is located at the central station 106. All of the data paths shown in FIG. 4 are multiplexed over a commercial cellular telephone link 509 and 104B which is connected to a public switched telephone network (PSTN) 105. The data paths include a data path 401 over which patient information is transferred to the central monitoring station, a two way voice channel 402 which interconnects the patient and the central monitoring station, and a data channel 403 which can be used by the clinician to send data and control signals to the portable unit 11.

Figure 5:
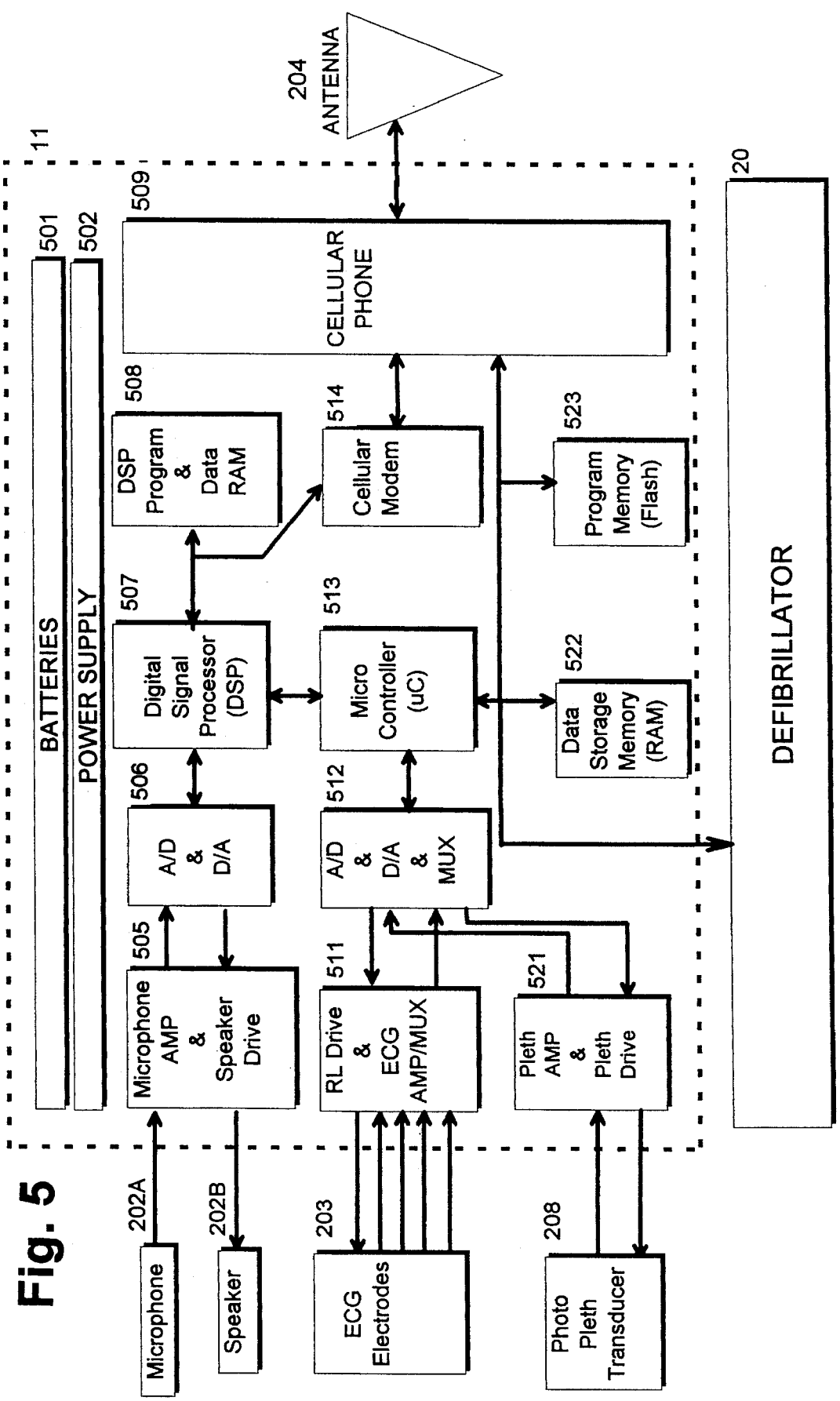
FIG. 5 is a block diagram of the monitoring device worn by the patient.

FIG. 5 is an overall block diagram of the monitoring, processing and communication unit 11 which is worn by the patient 10. As shown in FIG. 2 and in FIG. 5, unit 11 is connected to the microphone 202A, the speaker 202B, the ECG electrodes 203, the plethysmograph transducer 208, the defibrillator 207 and the antenna 204. The central components of unit 11 include digital signal processor 507, programmable micro controller 513, DSP program and data ram 508, data storage memory 522 and control program memory 523. The DSP processor 507, the programmable microcontroller 513 and the associated memory devices 508, 522, and 523 are in themselves conventional. It is the operations they perform and the manner in which they are connected and used to form a system that is relevant to the present invention. For example, the microcontroller 513 may for example be a 68HC16 microcontroller which is available from Motorola and the DSP processor 507 may be a 56001 DSP processor available from Motorola.

Signals from microphone 202A are amplified by unit 505, converted to digital signals by analog to digital converter 506 and then passed to digital signal processor 507. Signals directed to speaker 202B by digital signal processor 507 are converted to analog form by the digital to analog portion of circuit 506 and amplified by circuit 505 and then applied to speaker 202B. Circuits 505 and 506 are conventional circuits.

The ECG electrodes 203A to 203E (collectively referred to as 203) are connected to a RL (i.e. right leg) drive, ECG amplifier and multiplexer 511. Circuit 511 in turn supplies signals to and receives signals from analog to digital and digital to analog circuit 512. The RL drive, ECG amplifier and multiplexer 511 and the analog to digital, digital to analog circuit 512 are conventional.

The photo plethysmograph transducer 208 is connected to a plethysmograph amplifier and plethysmograph driver 521 which is conventional. Circuit 521 is in turn connected to analog to digital and digital to analog circuit 512.

Digital Signal Processor 507 is also connected to a cellular modem 514 which in turn is connected to a cellular phone 509. These are conventional components. For example cellular modem 514 may be an ATT V.32 bis, 14.4k bit modem with enhanced thru-put cellular (ETC) error correcting. The microcontroller 513 controls both the cellular phone 509, the digital signal processor 507 and the defibrillator 207.

The entire unit 11 is powered by a power supply 502 which is supplied by a battery 501. Battery 501 and power supply 502 are conventional. The overall control of the device, that is the sequencing and gating of information between the various units is under control of microcontroller 513 in a conventional manner.

Figure 6:
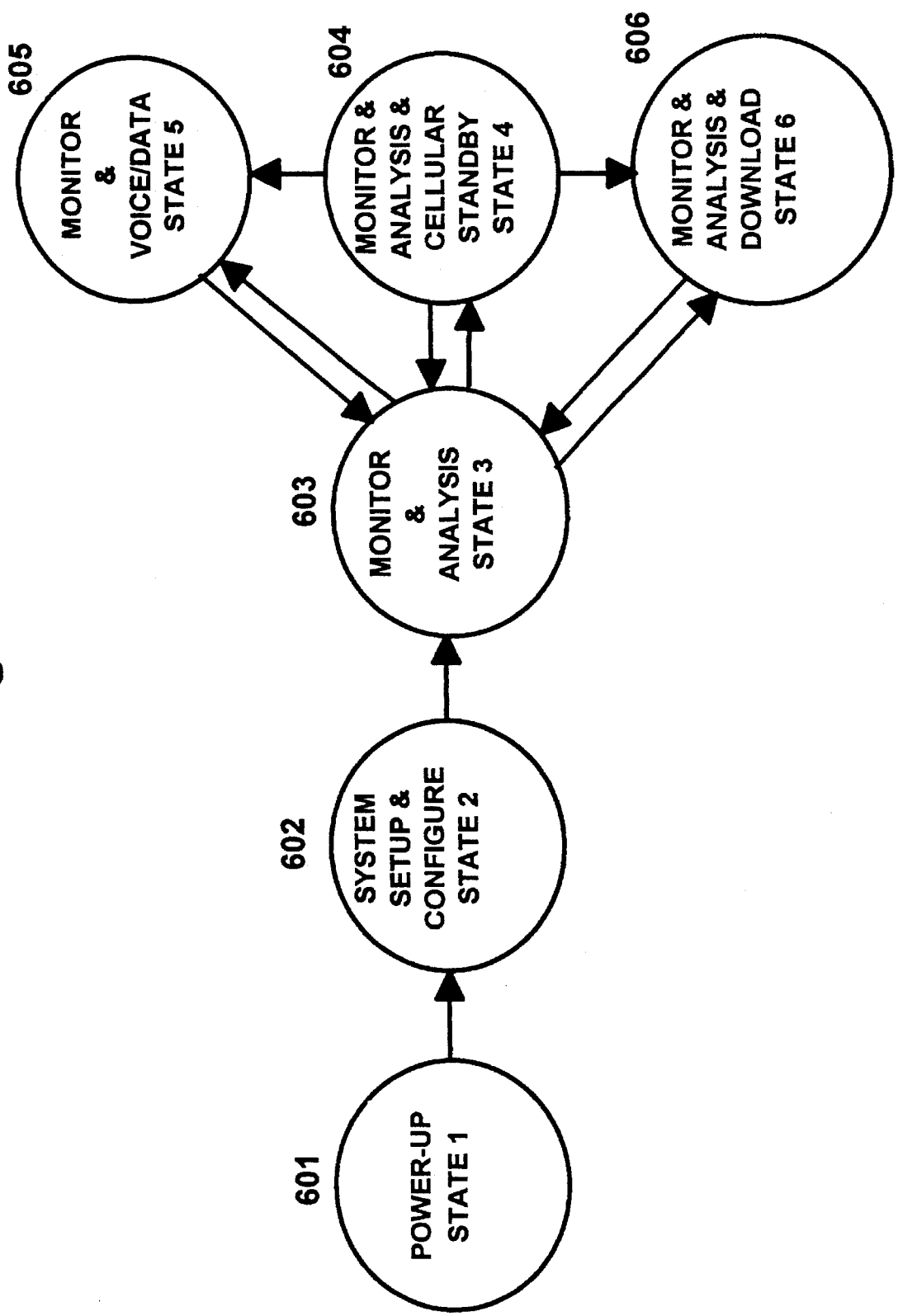
FIG. 6 is a state diagram showing the states in the operation of the device shown in FIG. 5.
Figure 7:
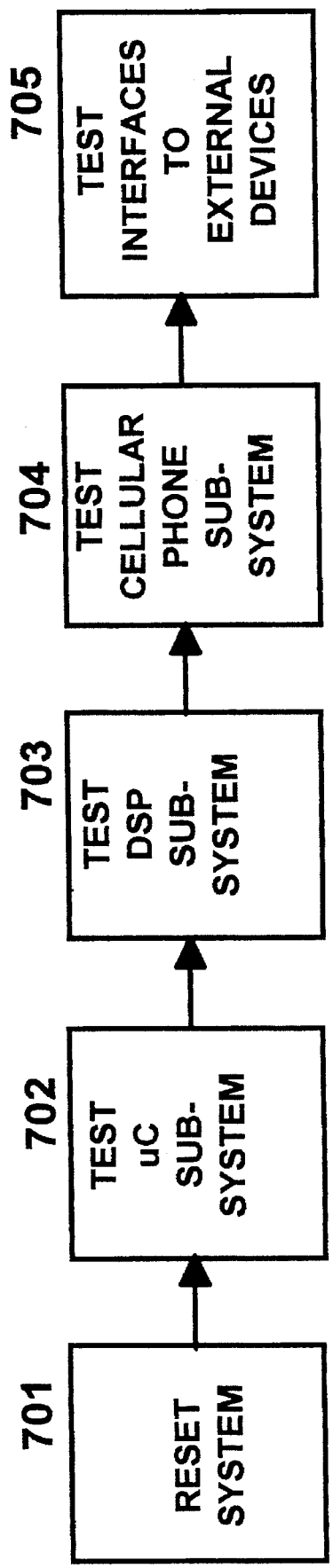
FIG. 7 is block diagram showing the operations that occur during state 1.
Figure 8:
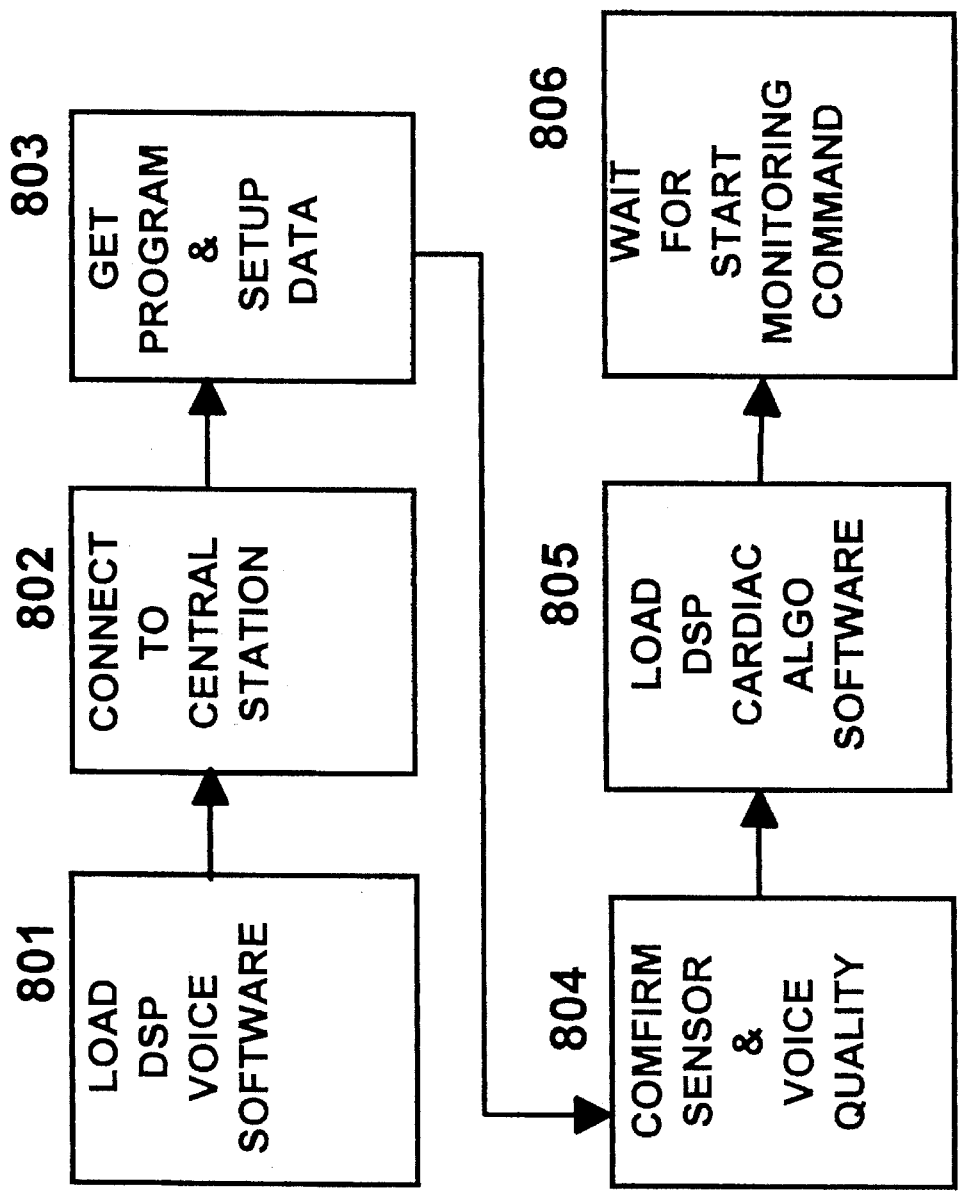
FIG. 8 is block diagram showing the operations that occur during state 2.

The operational states of device 11 are shown by FIG. 6 which is a state diagram. As indicated by circles 601 and 602, there is a conventional power up state 1 and a conventional system set up and configuration state 2. The operations which the system performs in these states is shown in FIGS. 7 and 8.

Figure 9:
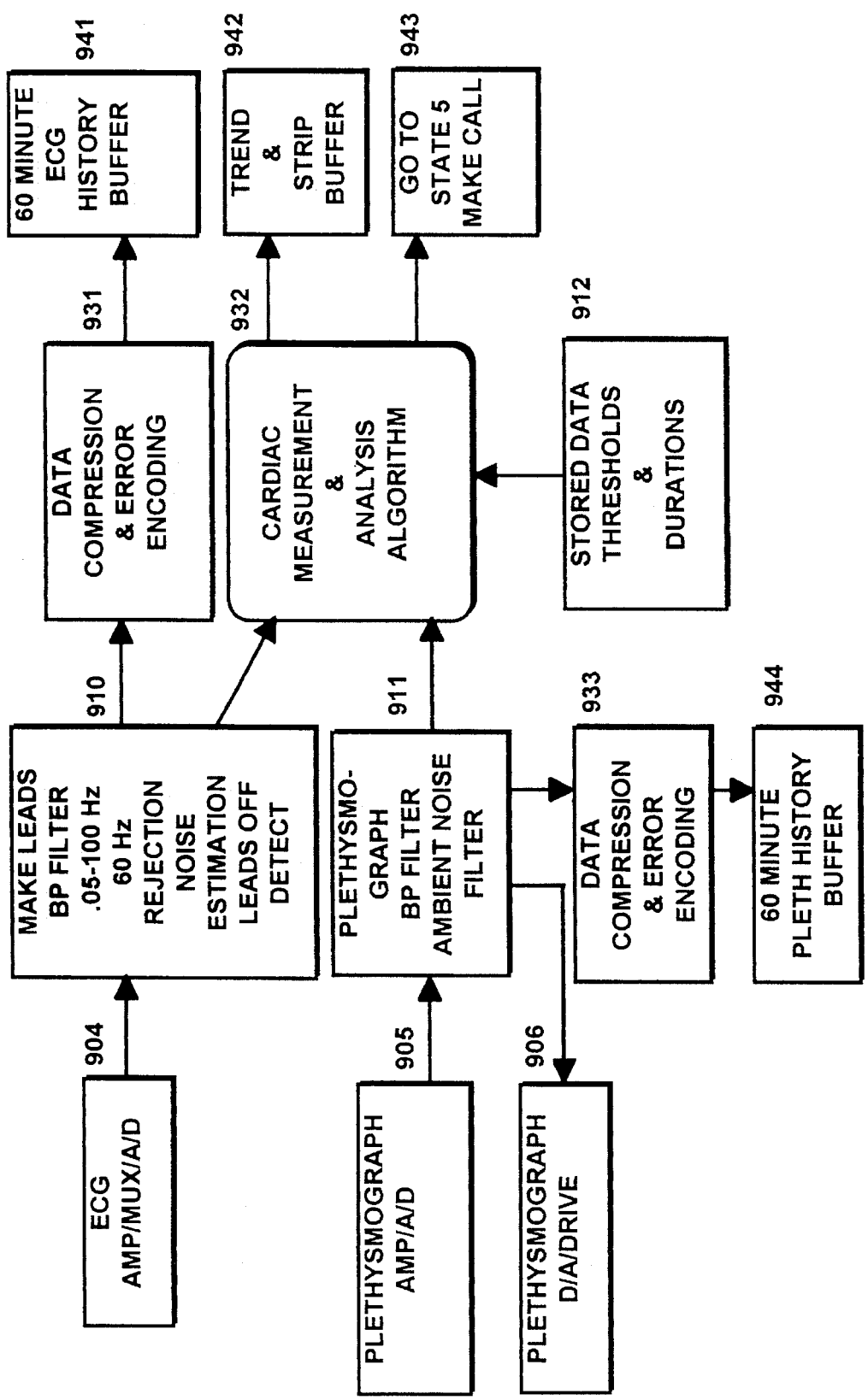
FIG. 9 is block diagram showing the operations that occur during state 3.

Most of the time the system is in state 3 which is illustrated by circle 603. In state 3 the system continuously monitors the patient's state. When unit 11 is in state 3 the measurements from the ECG 203 and the plethysmograph transducer 208 are constantly analyzed for life threatening conditions. If while in state 3 the system detects a warning or life threatening condition, the system immediately moves to state 5 illustrated by circle 605. When the system is in state 5, the system makes contact with the central facility. FIG. 9 shows the operations performed during state 3.

At a preset time each hour the system goes to state 4, illustrated by circle 604. In state 4 the system can receive a call from the central monitoring station. For example, in the preferred embodiment, the system is programmed to go to state 4 for five minutes every hour. While in state 4, the system continues the same monitoring operations as those performed in state 3. The system utilizes more power (i.e. more battery drain) in state 4 than in the more usual state 3, hence, the time in state 4 is minimized; however, the system is in state 4 for a sufficient amount of time so that the central monitoring station can contact the monitor and the patient if necessary.

In state 6, (circle 606) data is transmitted from the unit 11 to the central monitoring station 106. In state 6, the system continues to monitor the patient as in state 3; however, at the same time data is being downloaded from unit 11 to the central station 106.

FIG. 7 shows the operations that occur during state 1, that is, during power-up. First, as indicated by block 701, the entire system is reset. Next (block 702) a normal microcontroller diagnostic program is run to insure that the micro controller 513 is operating properly. Likewise (block 703) a normal diagnostic program is run to insure that the DSP processor 507 is operating properly, and the cellular phone 509 is checked (block 704). Finally, the interfaces to the defibrillator 207 is checked. The operations that take place in state 1 are conventional for this type of equipment.

When the system has completed the power up sequence it moves on to the system set up and configuration state, in state 2. The operations that occur in state 2 are conventional for this type of equipment. The operations that occur in state 2 are shown in FIG. 8. Initially block 801, the DSP voice software is loaded from program memory 513. The DSP software for handling voice communications is conventional and commercially available. Next, as indicated by block 802, unit 11 makes contact with the central station 106 and (block 803) operating programs and setup data are downloaded from the central station to unit 11. Next (block 804) the microcontroller 513 runs a subroutine which checks the quality of the signals the system is receiving from the modem and the ECG and photo-plethysmograph sensors. If the quality is not satisfactory, the unit 11 issues an audible alarm, sends an error message to the central station and remains in state 2. If the quality of signals is satisfactory, the unit 11 goes to block 805 and the DSP processor 506 is loaded with the cardiac analysis software which is normally stored in flash memory 523. At this point the system is ready to begin the monitoring operation. An "initiate operation command" is sent from the central station. When the initiate command is received the system moves into state 3 shown in FIG. 9.

State 3 is the main operating state of monitoring, processing and communicating unit 11. In state 3 the unit 11 is constantly monitoring the patient's condition. If a warning or life threatening abnormality is detected (block 943), the unit moves to state 5 and a call is placed to the central monitoring station. When the unit is in state 3, as indicated by block 904, the ECG signals are amplified, multiplexed and converted to digital signals. These operations are performed by the units 511 and 512 shown in FIG. 5. When the unit 11 is in state 3, the microcontroller 513 and the DSP processor 507 perform several normal ECG operations under program control (block 910). These include (a) the operation typically termed "make leads" which uses the data from the actual ECG electrodes to calculate other lead vectors (b) band pass filtering between 0.05 and 100 Hz, (c) 60 Hz rejection, (d) noise estimation, and (e) leads-off detection (to determine if a lead is disconnected). All of the operations represented by block 910 are conventional and it is noted that other conventional ECG operations in addition to those shown and discussed herein could also be performed by DSP unit 507 and microcontroller 513.

The results of the operations performed by block 910 go both to the cardiac measurement and analysis algorithm block 932 and to data compression and error encoding block 931. The operations in block 932 will be explained later with reference to FIGS. 13 and 14. The data compression and error encoding block 931 represents conventional operations which facilitate storing a 60 minute history of the patients condition (block 941). The data buffer (block 941) provides up to 60 minutes of previous patient history whenever the central station chooses to download the contents of the buffer. It is noted that the 60 minutes of history data indicated by block 941 is in fact stored in RAM memory 522. Block 905 indicates that signals from the plethysmograph transducer 208 are amplified and converted from analog to digital form. The digital signals pass to the microcontroller 513 and the DSP processor 507 which performs the operations shown in block 911. Namely, ambient noise is eliminated and the signals are band pass filtered. As indicated by block 906, conventional drive signals are provided to the plethysmograph transducer. The operation performed on the signals from plethysmograph transducer 906 are conventional operations and other operations could also be performed on the signals from the plethysmograph transducer.

The signals from block 911 go to measurement and analysis block 932 and to that compression block 933 and to 60 minute history buffer 944. As shown by block 912, the stored thresholds and durations are also provided to cardiac measurement and analysis block 932. The current trends and stored strips of the ECG are stored as indicated by block 942.

One of the most important aspects of state 3, is that when cardiac measurement and analysis operations indicated by block 932 indicate that a warning or life threatening event has occurred, the system moves to state 5 (block 943). In state 5 a call is made to the central monitoring station.

Figure 10:
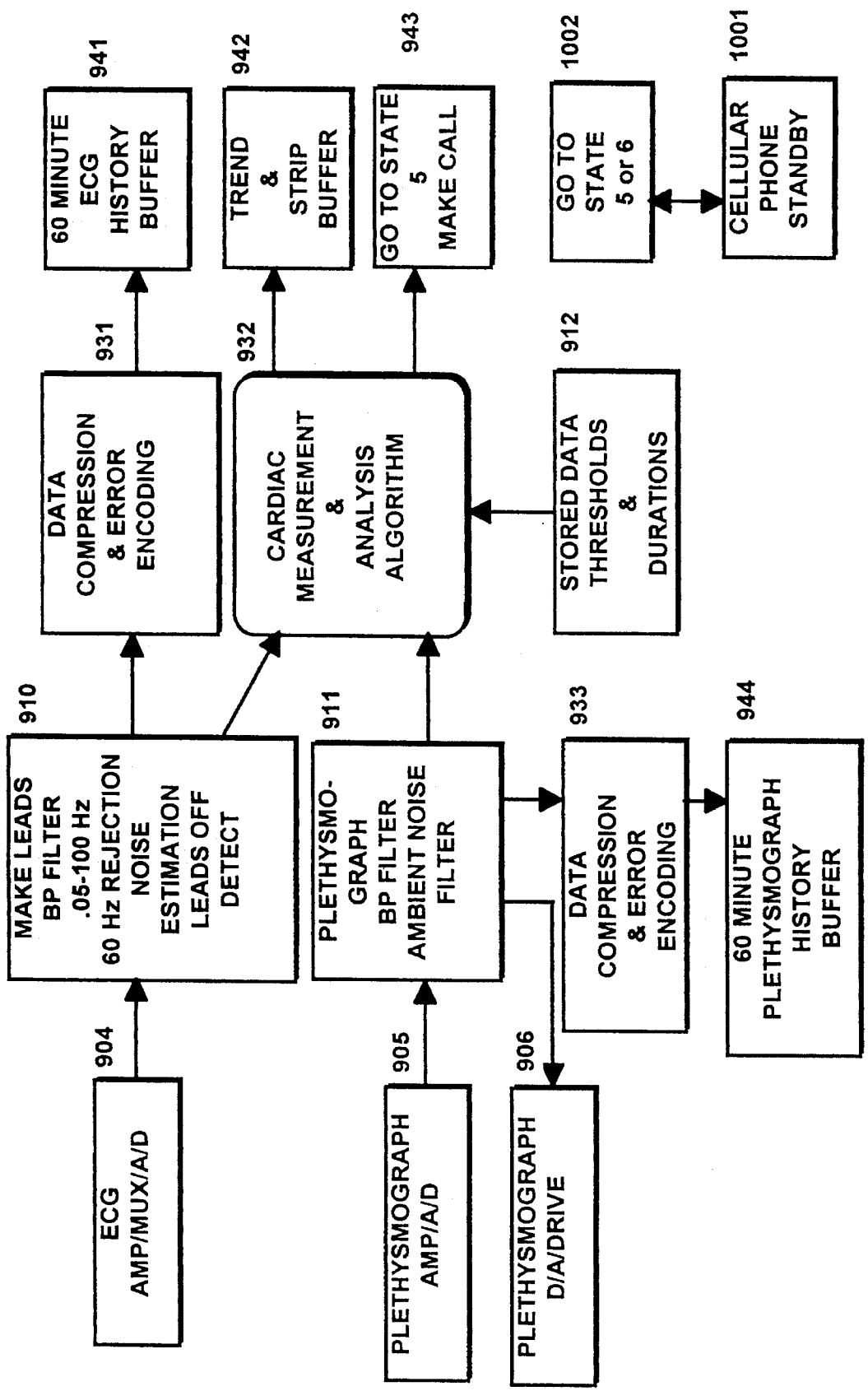
FIG. 10 is block diagram showing the operations that occur during state 4.

The operations that take place in state 4 are shown in FIG. 10. The operations in state 4 are identical to those in state 3 except that as indicated by blocks 1001, and 1002, the cellular phone 509 is in a "standby" or powered up state. In this state the unit can receive a call from the central station. If the unit does receive a call (block 1002), it will go to either state 5 or state 6 as directed by the call that is received.

Figure 11:
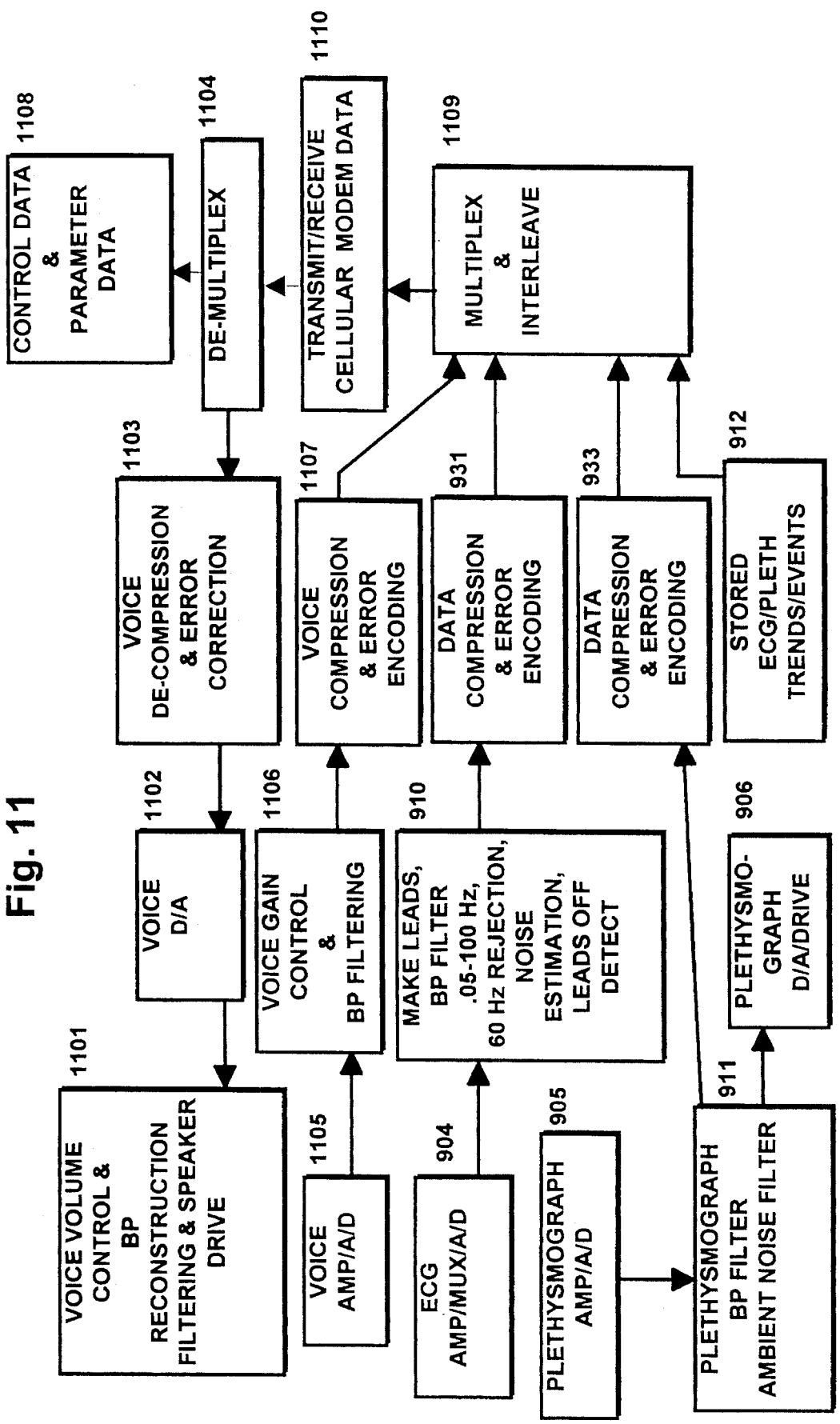
FIG. 11 is block diagram showing the operations that occur during state 5.

The operations in state 5 are shown in FIG. 11. State 5 is a state where the patient is in two way voice contact with the central monitoring station 106. Furthermore the data from the ECG and plethysmograph measurements is being compressed and transmitted to the central monitoring station 106 and the central station is able to send control data and parameter data to unit 11. As indicated by block 1110, data and voice are transmitted and received via the cellular modem 514 and the cellular phone 509. The data and voice are demultiplexed as indicated by block 1104. As indicated by blocks 1101, 1102 and 1103, the voice is decompressed and error corrected (block 1103), changed from digital to analog (block 1102), band pass filtered, volume controlled and sent to speaker 202B (block 1101). The voice signals from microphone 202A are amplified, converted to digital signals (block 1105) band pass filtered and volume controlled (block 1106) compressed and error, encoded (block 1107) multiplexed and interleaved (block 1109) and transmitted via the cellular modem 514 (block 1110). It is noted that the information received from modem 514 includes multiplexed voice and data information which is demultiplexed (block 1104). The voice is handled as previously explained. The data information includes control data and parameter data (block 1108). The parameter data is stored in RAM memory 522.

Figure 12:
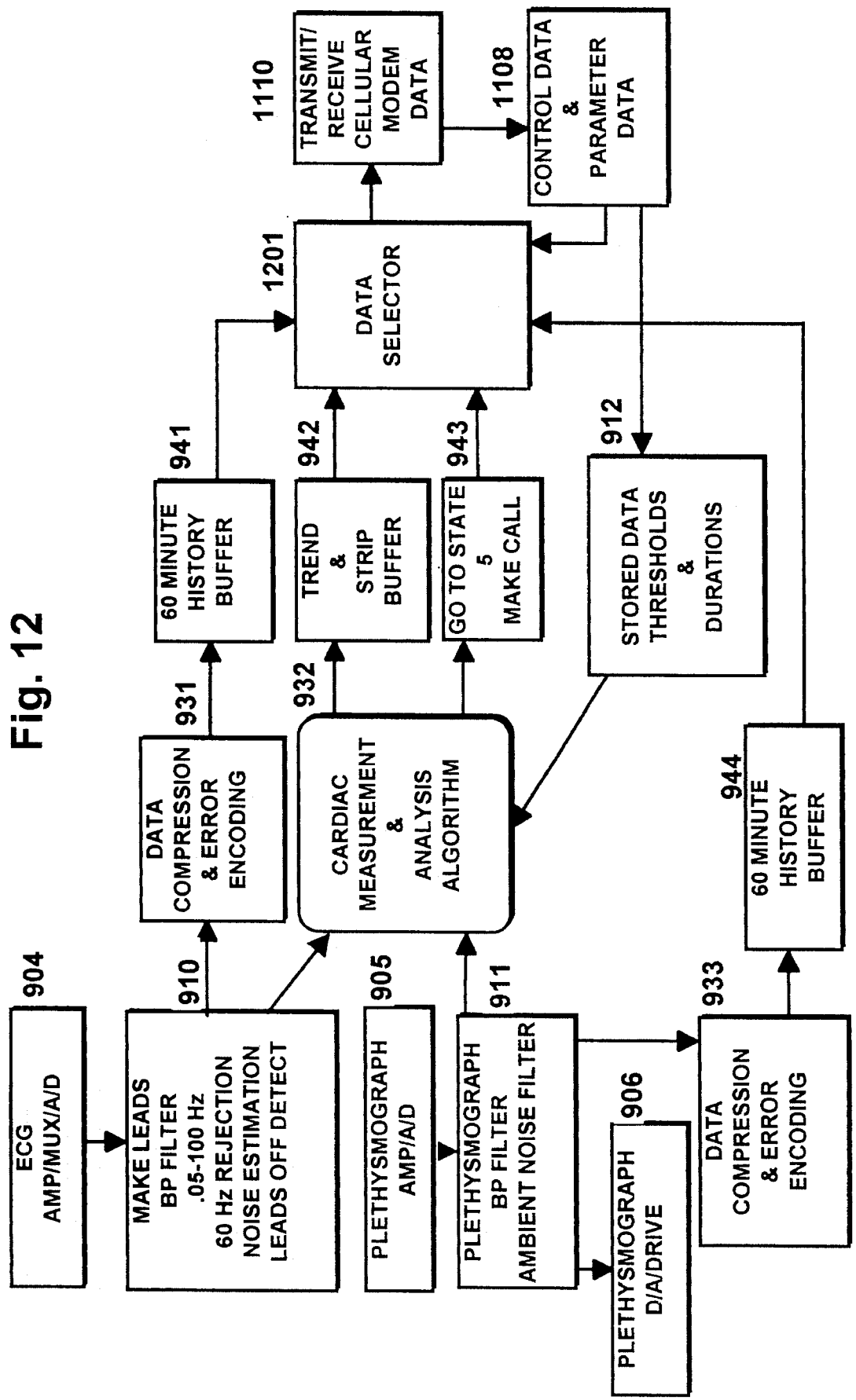
FIG. 12 is block diagram showing the operations that occur during state 6.

The operations that take place in state 6 are shown in FIG. 12. In addition to the operations that take place in state 3, the control data from block 1108 is used to select data for transmission (block 1201). In response to the control data received from block 1108, either the data which is stored in the 60 minute history (block 941), the trend and strip buffer (942), or the 60 minute plethysmograph buffer (block 944) are passed through the data selector (block 1201) and transmitted to the central station (block 1110) via the cellular phone 509. It is noted that with respect to the hardware shown in FIG. 5, all of the buffered information is stored in RAM memory 522 and the selection indicated by block 1201 is a selection made under program control by microcontroller 513. Furthermore, the various control commands are part of the data that is downloaded as indicated by block 1108.

Figure 13:
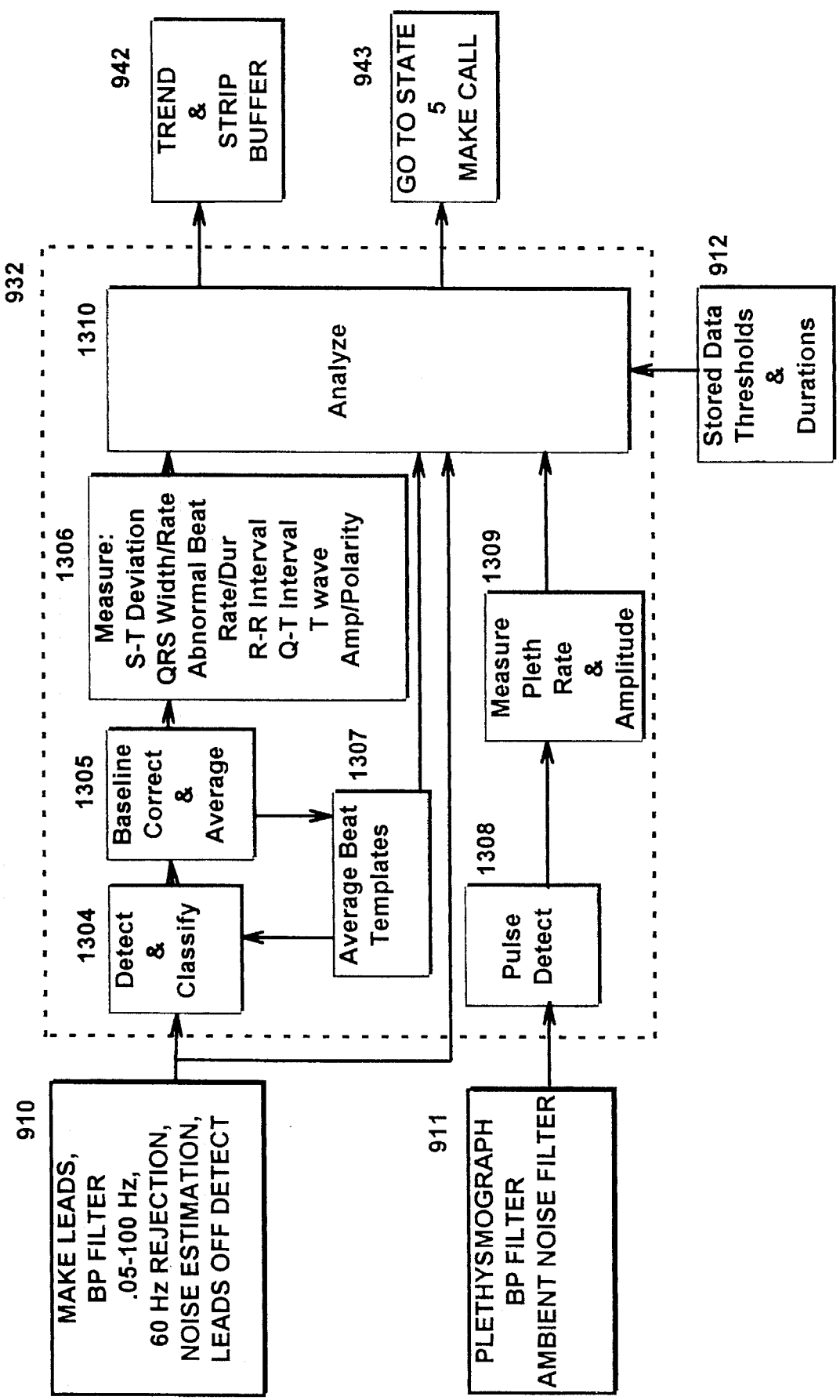
FIG. 13 is a block diagram that shows the programmed operations that take place during the Cardiac Measurement and Analysis step.

The details of the cardiac measurement and analysis algorithm operations (block 932) are shown in FIG. 13 and 14. It is noted that all of the operations shown in FIGS. 13 and 14 are controlled by stored programs and performed by digital signal processor 507 and microcontroller 513. The block 932 receives conditioned ECG lead data (block 910), conditioned plethysmograph data (block 911) and stored thresholds and durations (block 912). This is the ECG data that is conditioned as shown by block 910, the plethysmograph data that is conditioned as shown by block 911, and the historical data generated as indicated by block 912 are further processed as indicated by block 932. All of the operations shown in block 932 are programmed operations performed by DSP processor 507 and microcontroller 513.

The ECG data is handled in a conventional manner. First, the type of waveforms are detected and classified (block 1304). Next (block 1305) the baseline of the waveform is corrected and the beats are averaged, and finally the waveform is measured (block 1306). The baseline correction and averaging provides "average beat templates" that are used by the detection and classification process. Block 1306 provides the following data to the analysis block 1310: S-T deviation, QRS width and rate, Abnormal Beat Rate and Duration, RR interval, Q-T interval and T wave amplitude and polarity. These are all standard ECG measurements that are performed in accordance with the teaching in the prior art.

The conditioned plethysmograph data (from block 911) is pulse detected (block 1308) and the rate and amplitude of the pulses are measured (block 1309). The measurement (block 1306), the average beat templates (block 1307), the plethysmograph rate and amplitude (block 1309) and the stored data and threshold and weights (block 1303) goes to an analyze block or subroutine 1310. The details of analysis block 1310 are shown in FIG. 14. The output from analyses block 1310 can initiate a change to state 5 and a call to the central monitoring station (block 943) and it stores information in the trend and strip buffer (block 942).

The details of the programmed operations represented by block 1310 are shown in FIG. 14. The five inputs to block 1310, come from the blocks shown in FIG. 13. As indicated by block 1406, trends are detected in S-T Deviation, QRS width and rate, abnormal beat and duration, R-R interval, Q-T interval, T wave amplitude and polarity, plethysmograph amplitude and plethysmograph rate. The trends from block 1406 along with representative strips and templates are stored as indicated by block 1407. As indicated by block 1408 the key parameters are compared to stored threshold values. If any parameter exceeds the threshold for a specified duration, the system moves to state 5 which dials the cellular phone and notifies the central station. The parameters that are compared against stored threshold values are S-T deviation, QRS width and rate, abnormal beat rate and duration, R-R interval variability, Q-T interval, T wave amplitude and polarity, plethysmograph amplitude, and plethysmograph rate. Each parameter has stored in the stored data and thresholds 912, a threshold value and an allowable duration. If any parameter exceeds the threshold for the critical duration or if there is any type of general instrument error condition, the system moves to state 5 (block 943) and the central station is notified.

A block diagram of the central monitoring station 106 is shown in FIG. 15. The central monitoring station is controlled by a general purpose computer 1501. The station includes a display 1502 and a normal telephone 1503. Patient data is stored in a data memory 1505. The computer 1501 controls the data that is displayed on display 1502. A cellular modem and demultiplexer 1510 is connected to the regular telephone network and it provides data to the display 1502 and to the telephone 1503. Naturally it should be understood that the central monitoring station could be much more sophisticated and complex than the station shown in FIG. 15. FIG. 15 merely shows the elements of the central station that are pertinent to this invention. It is noted that the elements which form in the central station 106 are not of themselves novel and it is the manner that they are interconnected and used that is pertinent to the present invention.

While the particular therapeutic device which is shown in the preferred embodiment is a defibrillator, alternate embodiments use alternate therapeutic device including a drug infusion device that can be activated from the central station through unit 11 or a pacer which can be activated from the central station through unit 11.

The preferred embodiment shows an analysis device which is in effect a simple expert system which uses artificial intelligence, that is, a system which utilizes measurements and applies criteria to determine which action to take. Alternative embodiments can use more complex expert systems which consider many additional criteria.

The portable unit 11 in the preferred embodiment includes a cellular phone. It should be noted that alternatively the same advantages of patient mobility could be obtained by utilizing various other wireless wide area communication devices such as various digital networks that are now coming into widespread use.

While the invention has been shown with respect to preferred embodiments thereof, it will be recognized by those skilled in the art that various changes in form and detail may be made without departing from the spirit and scope of the invention. The invention includes all embodiments that are within the scope and breadth of the appended claims.

We claim:

1. A device adapted to be worn by a patient for transmitting data to a central monitoring station, said device comprising:

measurement means for measuring physiological parameters of the patient and for generating data representative of the measured parameters, analysis means for analyzing said data and for comparing the analyzed data to preset parameters and for generating an alarm signal when said data exceeds said preset parameters, wireless communication means connecting said device to said central monitoring station, means for initiating contact with said central monitoring station via said wireless communication means when said alarm signal is generated, so that said central station is notified without intervention by said patient when said alarm signal is generated;

the device including said measurement, analysis, communications and contact initiating means being packaged in a modular unit sized to be worn externally on a patient's arm and the unit including means for mounting the unit on the patient's arm;

the measurement means including at least one external sensor affixable to a sensing location on the patient's skin to detect at least one physiological parameter at a location spaced from the unit;

the wireless communication means including a speaker-microphone connected to the unit and adapted for mounting adjacent the patient's head for bidirectional voice communications with the central monitoring station;

said voice communications being enabled by said means for initiating contact with said central monitoring station; and the wireless communication means including means for multiplexed transmission and reception of both data and voice communications via a common channel.

2. The device recited in claim 1 wherein said measurement means includes an electrocardiogram.

3. The device recited in claim 1 wherein said measurement means includes a plethysmograph transducer.

4. The device recited in claim 1 wherein said measurement means includes an ECG and a plethysmograph transducer.

5. The device recited in claim 1 wherein said analysis means includes a digital signal processor.

6. The device recited in claim 1 wherein said wireless communication means comprises a cellular phone means.

7. The device recited in claim 6 wherein said cellular phone means includes means for simultaneously transmitting data and voice communication.

8. The device recited in claim 1 including means for controlling a therapeutic device which can be activated by a command received over said wireless wide area communication means.

9. A system for monitoring a patient including:

a central station and a portable monitoring unit, said central station including stored patient history data and first communicating means for communicating via a wide area public network, said portable monitoring unit being adapted to be attached to an arm of a patient and including:

a second communicating means for communicating via a wide area public network, monitoring means for monitoring physiological parameters of said patient, means for storing preset parameter limits for said physiological parameters, means for activating said second communicating means to automatically contact said first communicating means when the limits of said physiological parameters are reached and communicating the physiological parameters to the central station, a microphone for the patient to input voice communications to the central monitoring station;

means for multiplexing data representative of the monitored physiological parameters and of voice communications input via the microphone for contemporaneous transmission to the central monitoring station;

a speaker for the patient to listen to voice transmissions from the central monitoring station; and means for receiving and demultiplexing control or parameter data and voice communications from the central monitoring station for outputting the voice communications to the speaker.

10. A system according to claim 9 in which the first and second communicating means each include bidirectional cellular telephone receiving and transmitting apparatus and means for compressing and decompressing data representing the physiologic parameters and voice communications.

11. The system recited in claim 9 wherein said second communication means includes a cellular phone means.

12. A system for monitoring a patient including:

a central station and a portable monitoring unit, said central station including stored patient history data and first communicating means for communicating via a wide area public network, said portable monitoring unit being adapted to be attached to an arm of a patient and including:

a second communicating means for communicating via wide area public network, monitoring means for monitoring physiological parameters of said patient, means for storing preset parameter limits for said physiological parameters, means for activating said second communicating means to automatically contact said first communicating means when the limits of said physiological parameters are reached and communicating the physiological parameters to the central station, the first and second communicating means each including bidirectional cellular telephone receiving and transmitting apparatus and means for compressing and decompressing data representing the physiologic parameters.

* * * * *